US011122220B2

(12) United States Patent
Lam et al.

(10) Patent No.: US 11,122,220 B2
(45) Date of Patent: Sep. 14, 2021

(54) AUGMENTED VIDEO REALITY

(71) Applicant: Zyetric System Limited, Hong Kong (CN)

(72) Inventors: Pak Kit Lam, Hong Kong (CN); Peter Han Joo Chong, Hong Kong (CN)

(73) Assignee: Zyetric System Limited, Kowloon (HK)

( * ) Notice: Subject to any disclaimer, the term of this patent is extended or adjusted under 35 U.S.C. 154(b) by 0 days.

(21) Appl. No.: 16/526,491

(22) Filed: Jul. 30, 2019

(65) Prior Publication Data

US 2019/0379843 A1 Dec. 12, 2019

Related U.S. Application Data

(63) Continuation of application No. PCT/IB2018/000159, filed on Feb. 3, 2018.

(60) Provisional application No. 62/454,694, filed on Feb. 3, 2017.

(51) Int. Cl.
*H04N 5/272* (2006.01)
*H04N 5/262* (2006.01)
*H04N 7/14* (2006.01)
*H04N 7/15* (2006.01)

(52) U.S. Cl.
CPC ........... *H04N 5/272* (2013.01); *H04N 5/2628* (2013.01); *H04N 7/142* (2013.01); *H04N 7/147* (2013.01); *H04N 7/15* (2013.01); *H04N 2007/145* (2013.01)

(58) Field of Classification Search
USPC ..................................... 455/404.1; 348/14.08
See application file for complete search history.

(56) References Cited

U.S. PATENT DOCUMENTS

| 9,197,856 | B1* | 11/2015 | Tangeland | ........... H04N 5/2624 |
| 2011/0249075 | A1* | 10/2011 | Abuan | .................. H04N 7/147 |
| | | | | 348/14.02 |
| 2015/0002541 | A1* | 1/2015 | Dillavou | .............. G06T 19/006 |
| | | | | 345/633 |
| 2015/0213650 | A1* | 7/2015 | Barzuza | ............... H04N 13/332 |
| | | | | 348/14.07 |
| 2017/0098332 | A1* | 4/2017 | Knight | ...................... G06T 7/10 |
| 2019/0222806 | A1* | 7/2019 | Soppelsa | ................ H04N 5/272 |

FOREIGN PATENT DOCUMENTS

WO 2018/142222 A1 8/2018

OTHER PUBLICATIONS

International Preliminary Report on Patentability received for PCT Patent Application No. PCT/IB2018/000159, dated Aug. 15, 2019, 8 pages.
International Search Report and Written Opinion received for PCT Patent Application No. PCT/IB2018/000159, dated Jun. 6, 2018, 10 pages.

* cited by examiner

*Primary Examiner* — Maria El-Zoobi
(74) *Attorney, Agent, or Firm* — Morrison & Foerster LLP

(57) ABSTRACT

At an electronic device coupled to a display, a communication interface, and a first image sensor, first image data is captured from the first image sensor. Second image data is received over the communication interface from a first remote device. The display displays a portion of the second image data with a portion of the first image data. The displayed portion of the second image data obscures some of the first image data.

15 Claims, 13 Drawing Sheets

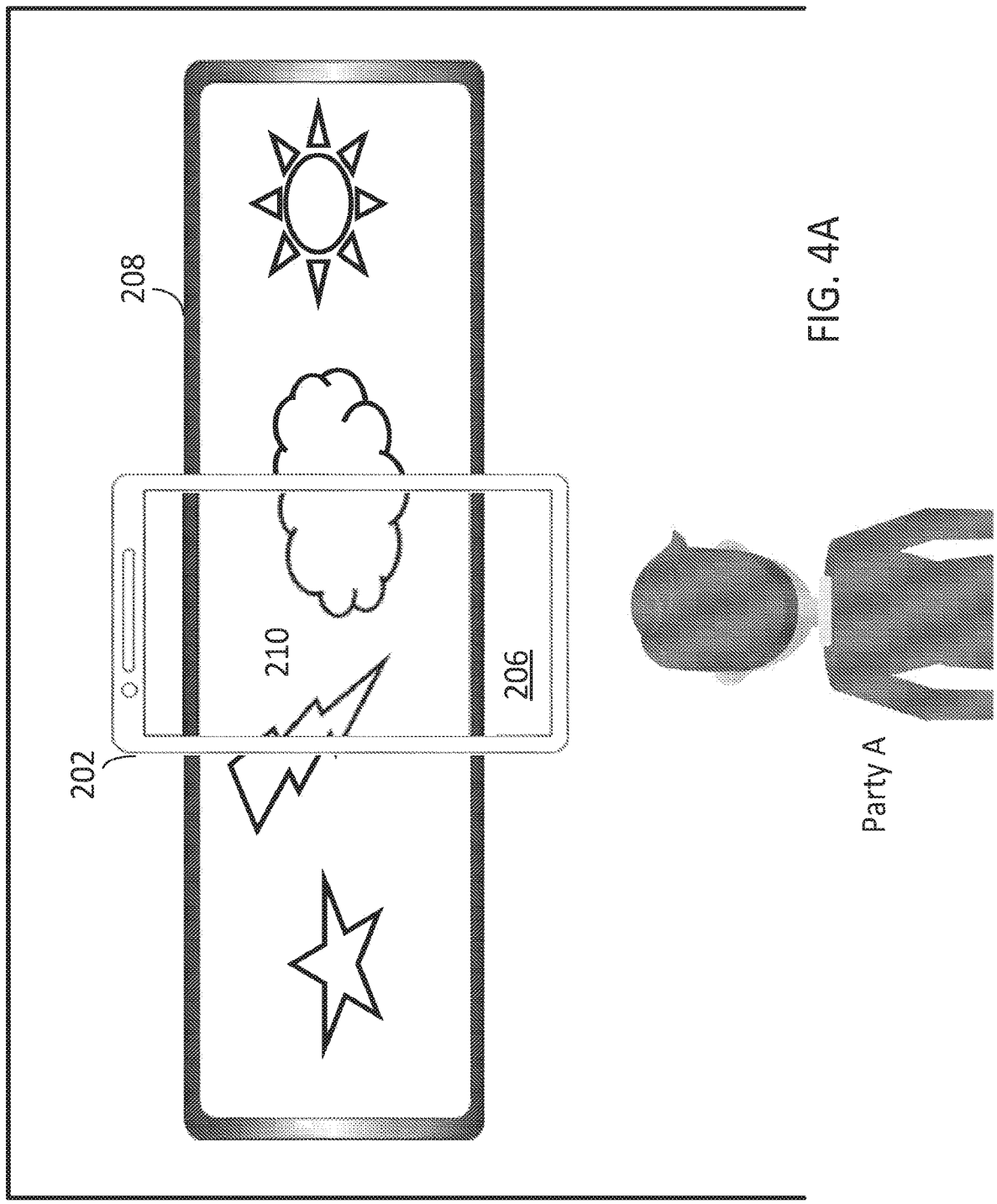

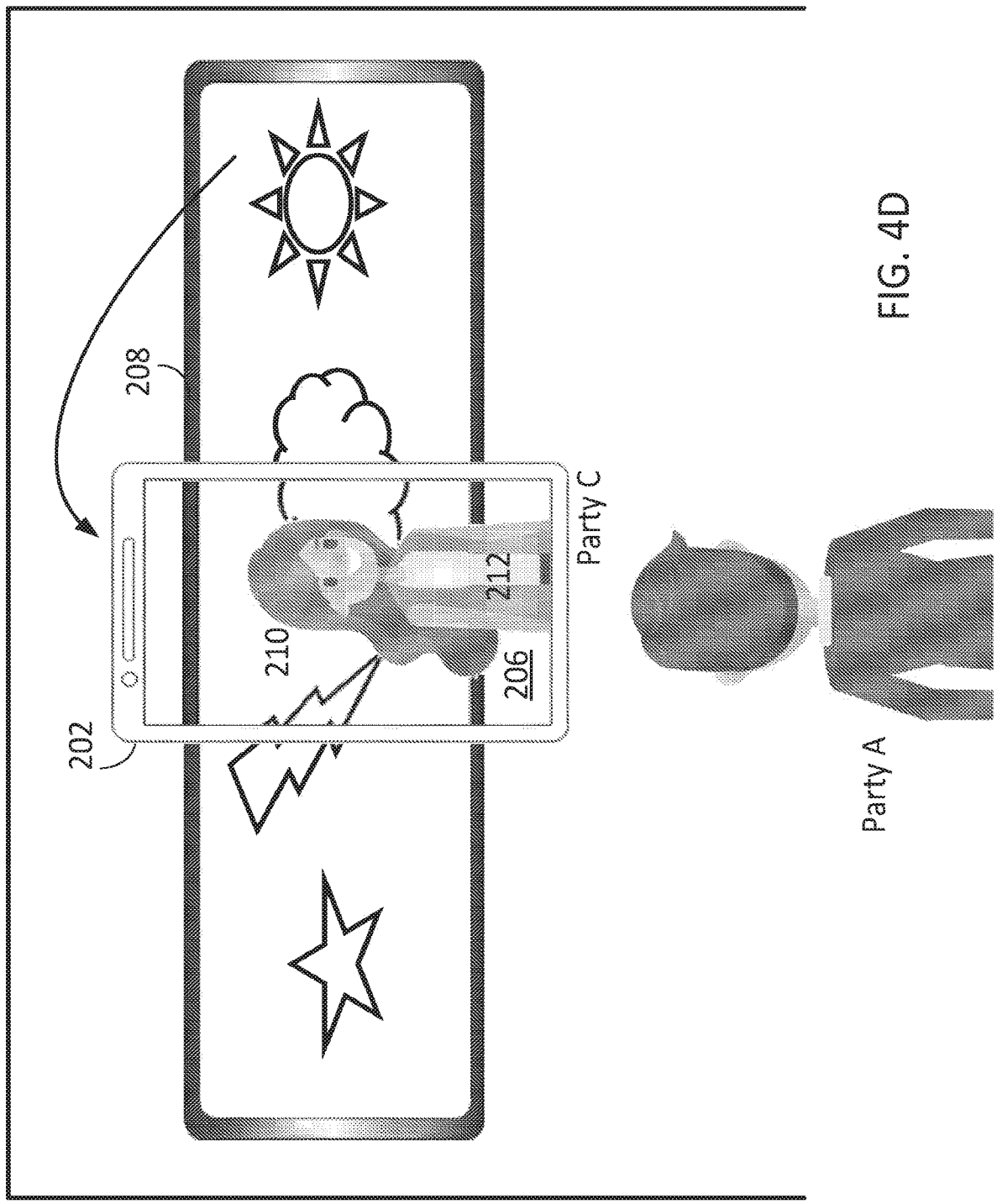

AUGMENTED VIDEO REALITY

CROSS-REFERENCE TO RELATED APPLICATIONS

This application is a Continuation of International Application No. PCT/IB2018/000159, filed Feb. 3, 2018, which claims priority to and the benefit of U.S. Provisional Patent Application Ser. No. 62/454,694, entitled "Augmented Video Reality", filed Feb. 3, 2017, the content of which is hereby incorporated by reference for all purposes.

FIELD

The present disclosure relates to augmented reality and, more specifically, to augmented reality as applied to video.

BACKGROUND

Video communication is a ubiquitous form of communication today. Electronic devices from mobile phones and tablets to large, complex video conferencing systems enable all sorts of users to communicate over video in many different contexts. These devices typically include cameras, microphones, and video screens that capture, transmit, and display image and/or audio to and from another device or system.

SUMMARY

In some embodiments of the present technology, a smart device is connected to a camera (e.g., an internal or external camera). The smart device includes a display and a communication interface. The smart device receives image data of a remote user over the communication interface. The smart device also captures image data of the environment behind the display using the camera. The smart device then displays a portion of the image data of the remote user overlaid on the image data of the environment so that it appears virtually that the remote user is in the environment of the smart device. The smart device may also be connected to a front-facing camera so that image data of the user of the smart device can be transmitted to the smart device of the remote user. This allows the user of the smart device to appear virtually in the remote user's environment on the display of the remote user's smart device.

BRIEF DESCRIPTION OF THE FIGURES

The present application can be best understood by reference to the figures described below taken in conjunction with the accompanying drawing figures, in which like parts may be referred to by like numerals.

FIGS. 4A-4E depict an embodiment of the present technology for multi-party conference calls.

DETAILED DESCRIPTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the present technology. Thus, the disclosed technology is not intended to be limited to the examples described herein and shown, but is to be accorded the scope consistent with the claims.

Embodiments of the present technology allow two or more parties, located in different parts of the world, involved in, for example, a video conference call or an online game, to perceive that they are all meeting or playing in the same room. Below, a non-limiting example of conference calling is described to illustrate how augmented video reality perception works in some circumstances.

Some embodiments of the present technology provide for an improved video conference environment by making the video conference experience more seamless. This improves the quality of communication among participants and improves the man-machine interface by making video conferencing a more natural and intuitive way to communicate. In contrast, other video conference systems may provide for less than optimal communication among participants because such systems make communication more awkward by emphasizing that participants are not present in the same room (e.g., by showing distracting backgrounds of a remote participant to a local user). Some embodiments of the present technology address this deficiency by displaying a combination of portions of video of remote one or more remote participants with portions of video of the local environment of a local participant.

Figure 1B:
FIGS. 1A-1B depict an exemplary electronic device that implements some embodiments of the present technology.
Figure 1A:
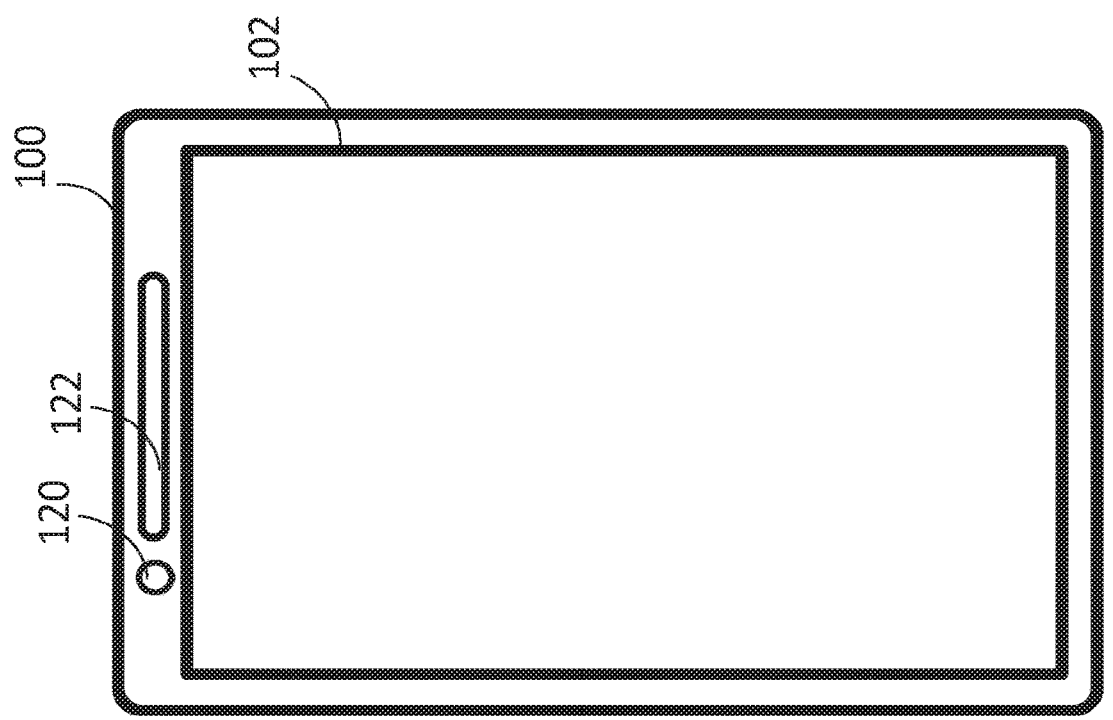

FIGS. 1A-1B depict smart device 100 that optionally implements some embodiments of the present technology. In some examples, smart device 100 is a smart phone or tablet computing device but the present technology can also be implemented on other types of specialty and non-specialty electronic devices, such as wearable devices, cameras, a laptop computer, a desktop computer, a television, a display, or a monitor. In some embodiments smart device 100 is similar to and includes components of computing system 500 described below in FIG. 5 or alternatively is connectable to such components external to the device. Smart device 100 includes display 102 (which, in some cases, can be a touch sensitive display) and back-facing camera 124. Smart device 100 also includes front-facing camera 120 and speaker 122. Smart device 100 optionally also includes other sensors, such as microphones, movement/orientation sensors (e.g., one or more accelerometers, gyroscopes, digital compasses, etc.), depth sensors (which are optionally part of camera 120 and/or camera 124), etc.

Other variations of smart device 100 relevant to the current technology include smart devices that do not contain the above components (or the components of computing system 500) integrated into a single unit (e.g., a single housing/support structure) but instead are connected together using wired, wireless, or other communication techniques. For example, in other variations of smart device 100, a back-facing camera and/or a front-facing camera may be external to the unit that contains the display. As another example, a microphone and other I/O device may be a part of the smart device or may be physically separate but in communication with the smart device (e.g., a microphone may be a part of the smart device or may be present/integrated in the physical room and is communicatively coupled to the smart device). Additionally, any computing resources (e.g., a processor, memory, display device, etc.) that are necessary to perform the techniques described below may be integrated within the same unit with the display or be external to the display unit but are in communication with the display unit.

Figure 2A:
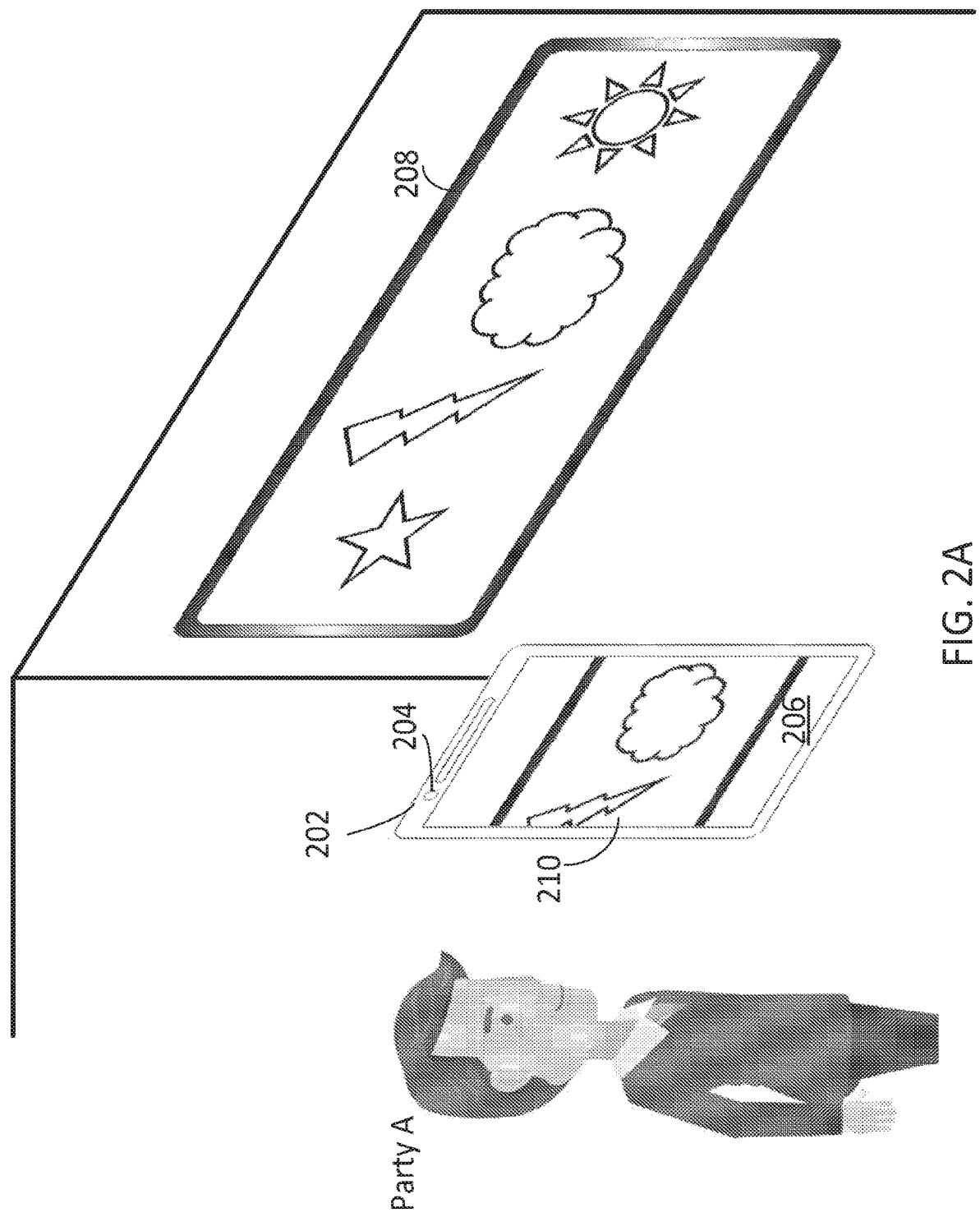
FIGS. 2A-2D depict an embodiment of the present technology applied to 2-way conference calling.
Figure 2B:
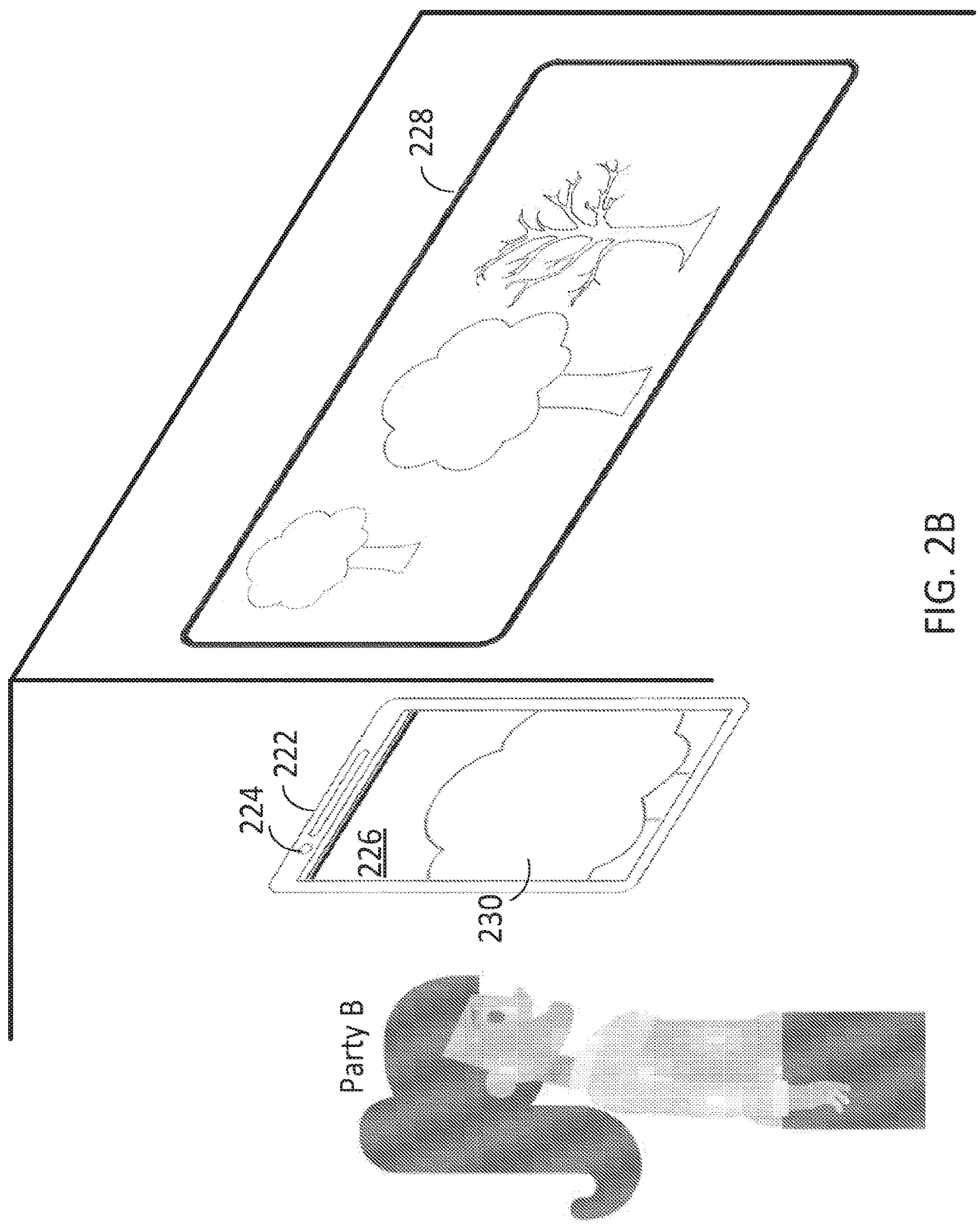

In one example, an embodiment of the present technology facilitates a 2-party conference call between Party A and Party B. Each party has a smart device to enable the conference call, such as a smart device describe with respect to FIGS. 1A-1B. FIGS. 2A and 2B depict Party A and Party B, respectively, and their associated devices.

In FIG. 2A, Party A is looking at smart device 202 prior to the conference call with Party B (e.g., the conference call application is running but a connection with Party B has not commenced or Party B is not yet in front of the camera of the remote device at the remote location). Smart device 202 may be smart device 100 described above with respect to FIGS. 1A-1B. Smart device 202 has front-facing camera 204 and display 206. Smart device 202 also has a back-facing camera aimed at background 208 of the room where Party A and smart device 202 are located. Display 206 is displaying image 210 of background 208 (from the back-facing camera). In cases where Party A and smart device 202 are in a room, background 208 may be decorations on a wall, the wall itself, a window, furniture, etc. Other backgrounds are also possible depending on where Party A and smart device 202 are located (e.g., the background may be the sky, mountains, trees, etc. when Party A and smart device 202 are outside or the background may include other people when Party A and smart device 202 are in a location with people present in or moving through the field of view of the back-facing camera).

In FIG. 2B, Party B is looking at smart device 222 prior to the conference call with Party A (e.g., the conference call application is running but a connection with Party A has not commenced or Party A is not yet in front of the camera of the remote device at the remote location). Smart device 222 has front-facing camera 224 and display 226. Smart device 222 also has a back-facing camera aimed at background 228 of the room where Party A and smart device 222 are located. Display 226 is displaying image 230 of background 228 (from the back-facing camera). In cases where Party A and smart device 222 are in a room, background 228 may be decorations on a wall, the wall itself, a window, furniture, etc. Other backgrounds are also possible depending on where Party A and smart device 222 are located (e.g., the background may be the sky, mountains, trees, etc. when Party A and smart device 222 are outside or the background may include other people when Party A and smart device 222 are in a location with people present in or moving through the field of view of the back-facing camera).

In the present example with respect to FIGS. 2A-2D, both parties see video of the other party and send video from the front-facing camera to the other party. In other examples of embodiments of the present technology, only one party sends video of the front-facing camera without receiving/displaying video and the other party only receives/displays video without sending their own video from the front-facing camera.

Returning to the example where Party A and Party B both send and receive video, in FIG. 2B, front-facing camera 224 of smart device 222 used by Party B captures a video image of Party B. In some cases, the video of Party B is captured in a way that excludes the background behind Party B (e.g., the background is trimmed out). In other cases, the video of Party B is captured to include the background. Optionally, smart device 222 then processes the video to remove the background. For example, smart device 222 performs image processing on the video to determine the outline of Party B and masks the video according to that outline. As another example, if front-facing camera (or another sensor) provides depth information, then device 222 can use that information to crop the video based on parts of the image with at a depth different than the depth associated with Party B. Other techniques, such as image processing techniques, can also be used. After capturing and optionally processing the video from front-facing camera 224, device 222 sends video to device 202 of Party A (FIG. 2A). The video that is sent to device 202 may or may not have the background cropped out. If the background is not cropped out, device 202 may remove/mask out the background using similar techniques as discussed above with respect to device 222 (or device 202 may use completely different techniques).

Figure 2C:
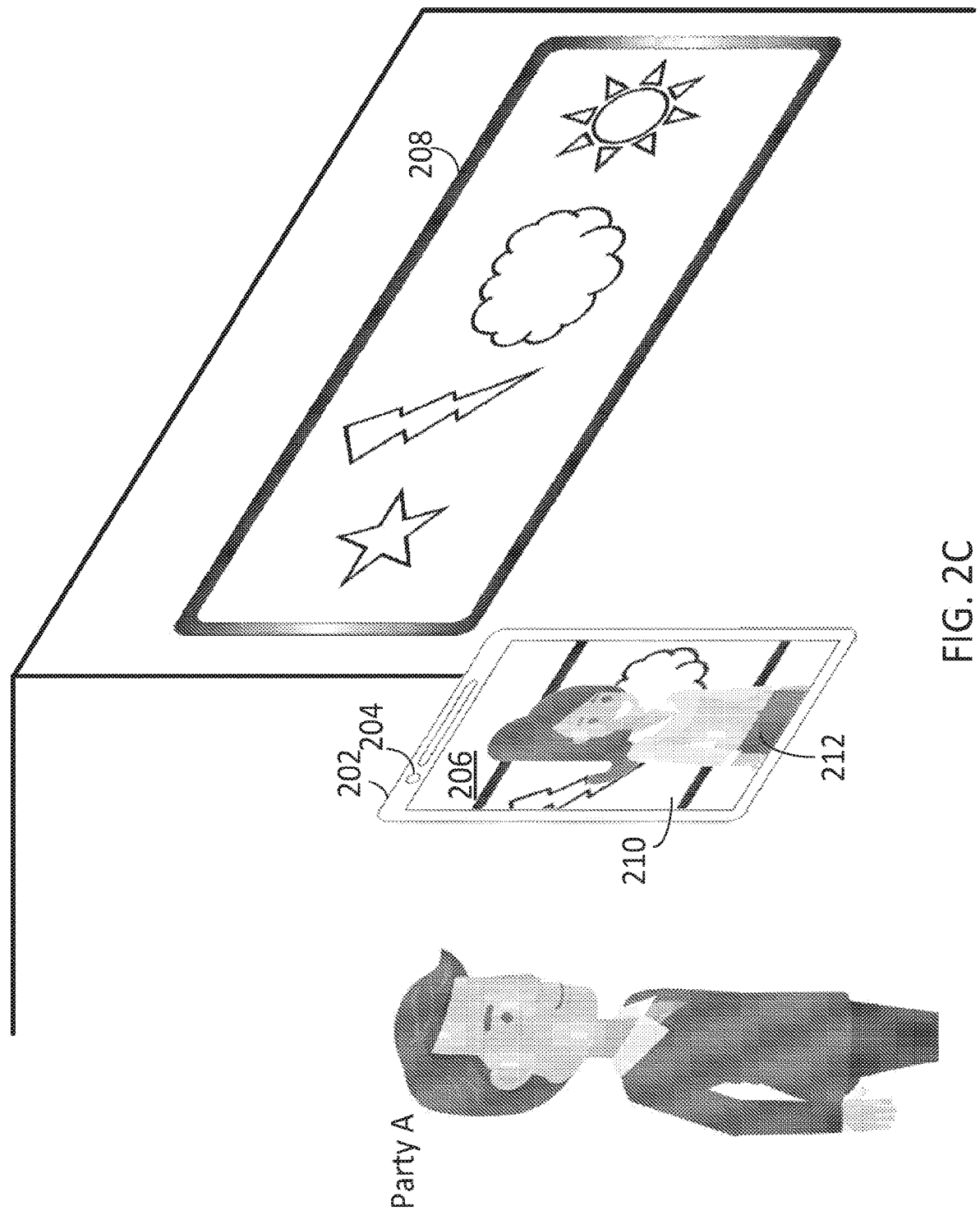

As depicted in FIG. 2C, once Party A's smart device 202 receives the video from Party B (and optionally processes it, such as removing the background), it overlays video 212 (which is a portion of or all of the received video) onto image 210 of background 208 as captured by back-facing camera of smart device 202 (e.g., instead of overlaying computer graphics onto a background as the traditional augmented reality technology does, i.e., embodiments of the current technology overlays the real-time image of a remote object onto the real image of background). In this manner a portion of the received video and a portion of the video of the background are combined and displayed together.

Optionally, smart device 202 can also process the received video data and/or process its own video data of the background as captured from back smart device 202's back-facing camera. For example, the received video data may contain depth information or other dimensional data that allows for the proper sizing of the video when displayed on smart device 202. For example, smart device 202 may determine the distance to background 208 and/or the distance to Party B (e.g., using depth sensors, distance sensors, or preset values) and use one or both of these distances to properly scale video 212 and/or image 210 of background 208 so that the combined image produces the most realistic image possible. This allows for more immersive video conferences and improves communication between Party A and Party B. Alternatively, smart device 202 can provide a user interface to allow Party A to scale the video of Party B and/or the video of the background.

Figure 2D:
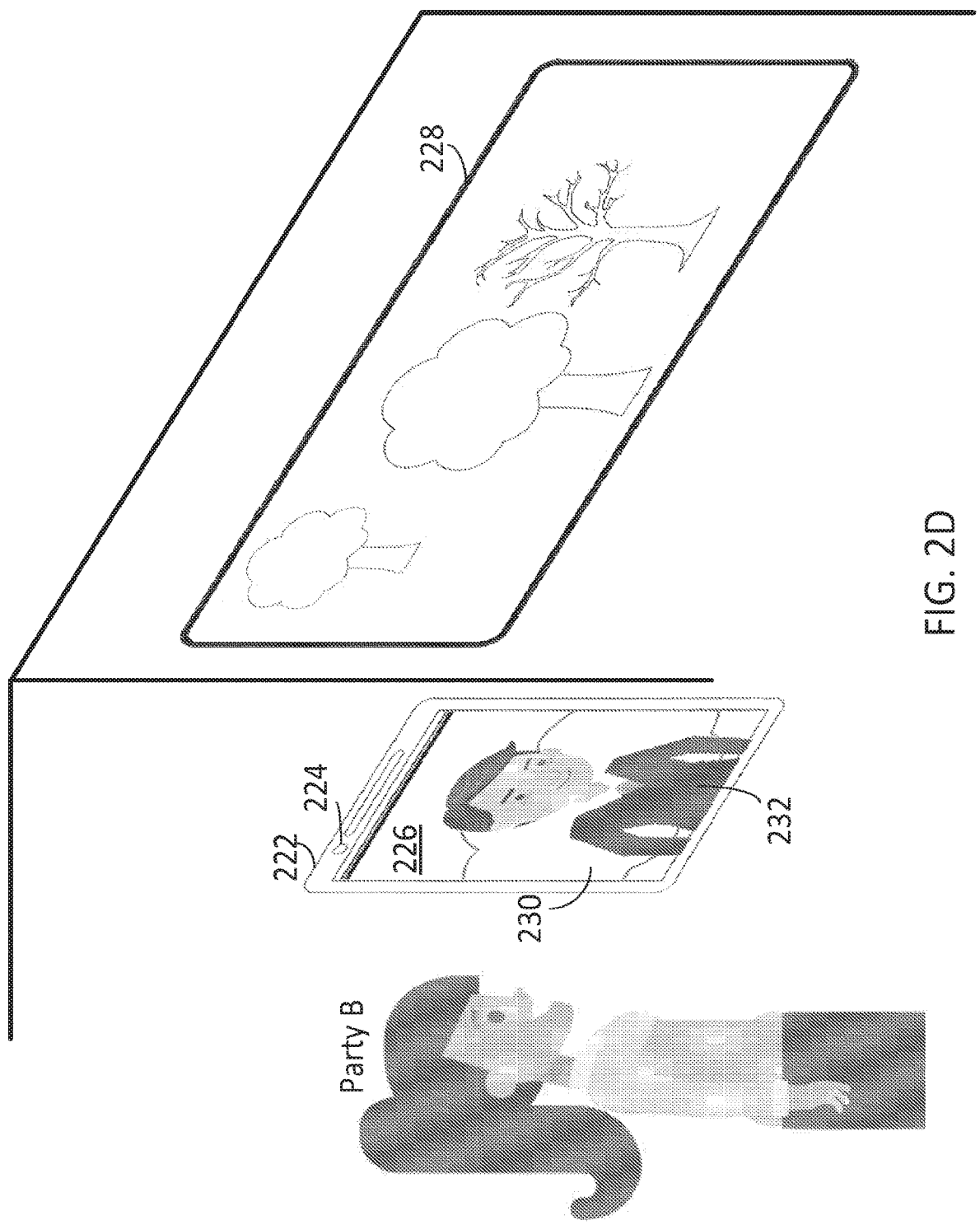

A similar process happens with respect to video captured of Party A (and Party A's background) from front-facing camera 204 of smart device 202. The video (cropped or uncropped) is sent to Party B's smart device 222. As depicted in FIG. 2D, smart device 222 (after optionally processing the video) displays video 232 overlaid on image 230 of background 228 as seen by the back-facing camera.

Figure 3A:
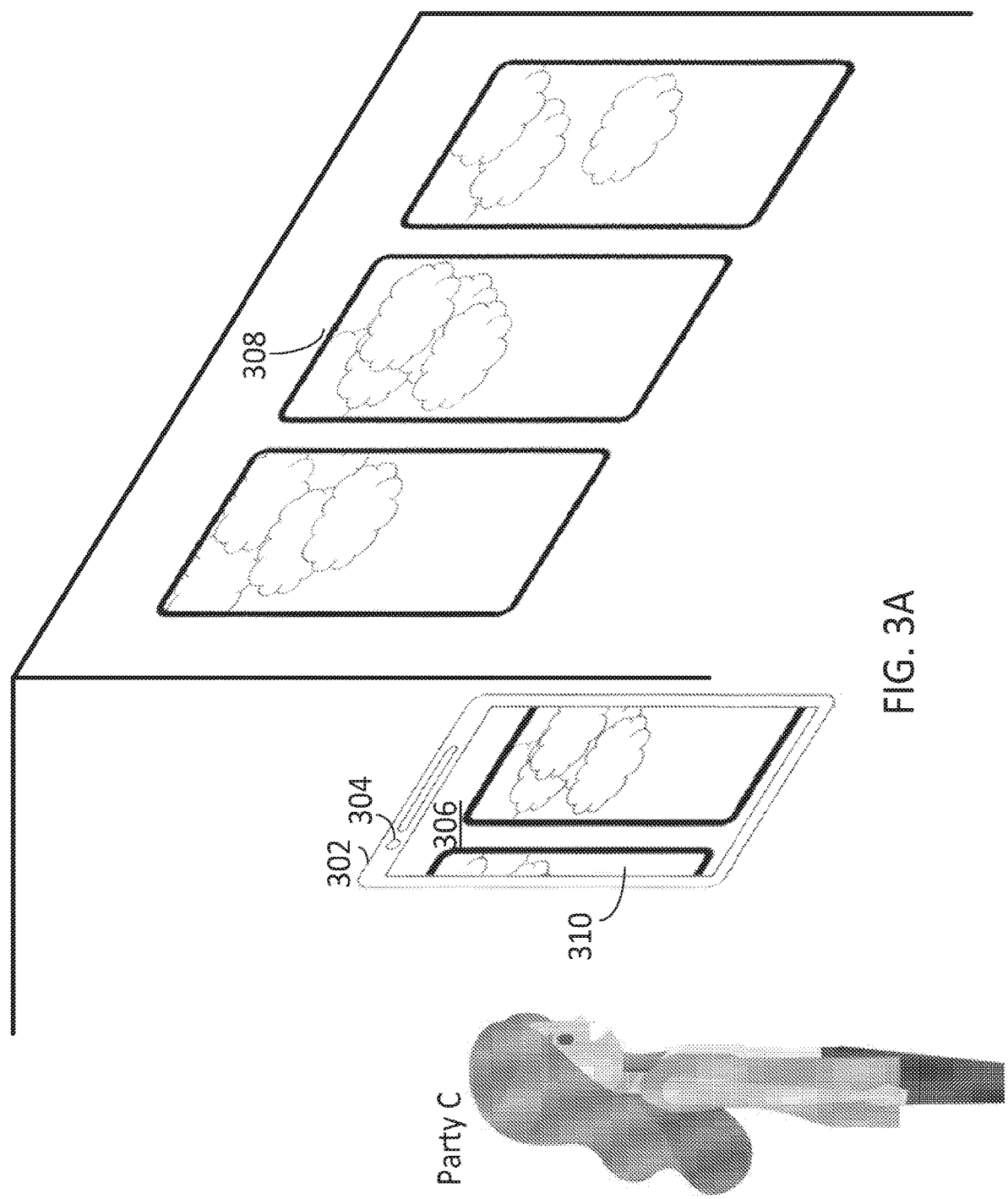
FIGS. 3A-3B depict an embodiment of the present technology applied to a 3-way conference call.
Figure 3B:
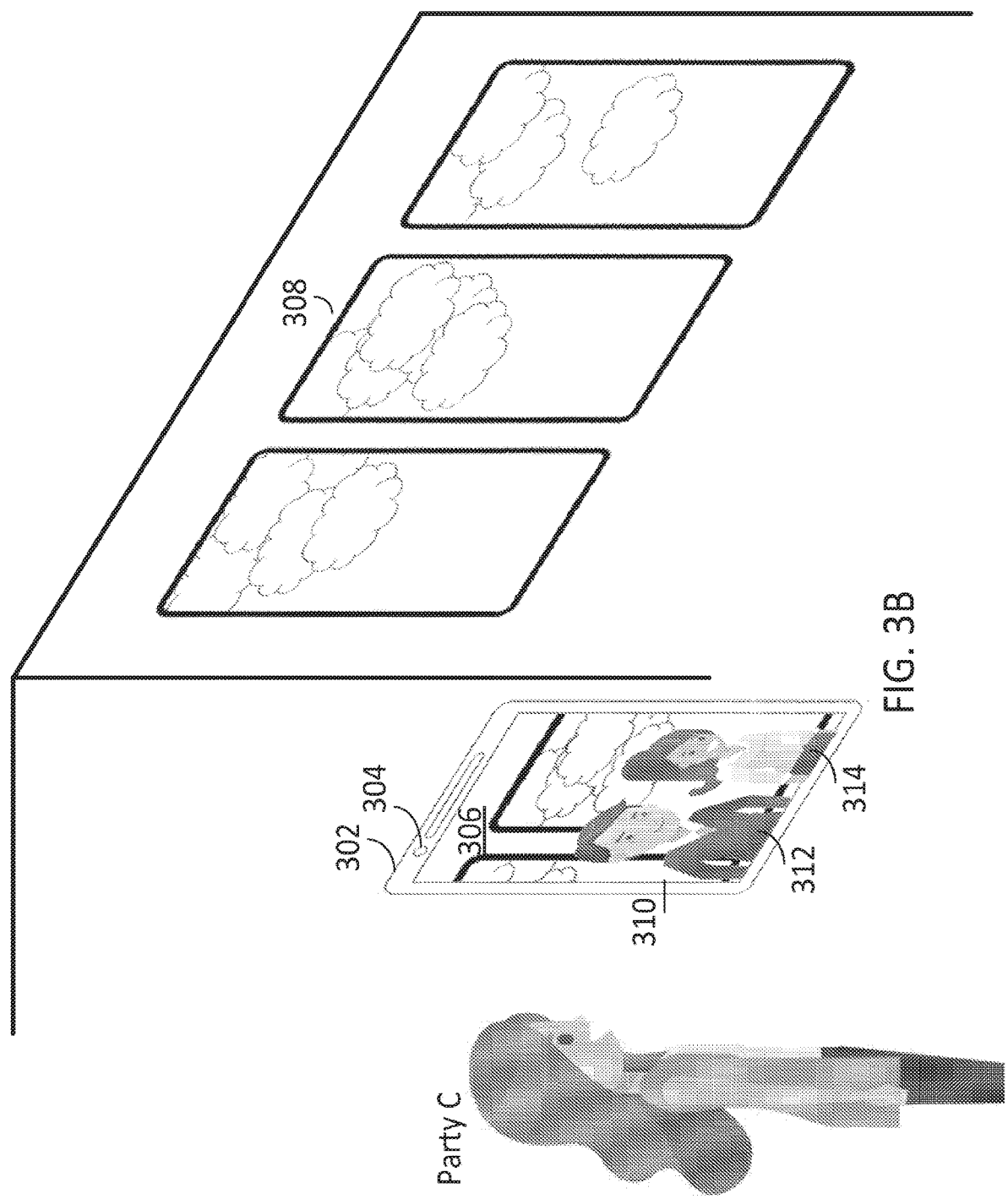

The same concept described with respect to FIGS. 2A-2D can be extended to more than 2-party conference calls. In the example of FIGS. 3A-3B, Party A, Party B and Party C are having a conference call between them. All three of them are equipped with a smart device or other device with a large display and both front-facing and back-facing cameras, such as devices described with respect to FIGS. 1A-1B, 2A-2D, or 5.

In FIG. 3A, Party C is looking at smart device 302 prior to the conference call with Party A and Party B (e.g., the conference call application is running but a connection has not commenced or the other parties are not yet in front of the camera of the remote device at the remote location). Smart device 302 has front-facing camera 304 and display 306. Smart device 302 also has a back-facing camera aimed at background 308 of the room where Party A and smart device 302 are located. Display 306 is displaying image 310 of background 308. In cases where Party 3 and smart device 302 are in a room, background 308 may be decorations on a wall, the wall itself, a window, furniture, etc. Other backgrounds are also possible depending on where Party C and smart device 302 are located (e.g., the background may be the sky, mountains, trees, etc. when Party C and smart device 302 are outside or the background may include other people when Party C and smart device 302 are in a location with people present in or moving through the field of view of the back-facing camera).

Using image data (still or video) from the back-facing camera, Party C will see background 308 of the room on display 304, such as shown by image 310 of FIG. 3A. Video of Party A and Party B are captured and optionally processed by smart devices 202 and 222, respectively, as described above with respect to FIGS. 2A-2D. In addition to sending video to and from smart devices 202 and 222, these devices also send their respective captured video to smart device 302 (and optionally could each receive video from smart device 302).

As depicted in FIG. 3B, once Party's C smart device 302 receives the video data from Party A and Party B (and optionally processes the data, such as cropping/removing the background from one or both videos and/or scaling the video), smart device 302 overlays video 312 (associated with Party B) and video 314 (associated with Party A) onto image 310 of background 308 as captured by back-facing camera of smart device 302 (e.g., instead of overlaying computer graphics onto a background as the traditional augmented reality technology does, i.e., embodiments of the current technology overlays the real-time image of a remote object onto the real image of background). In this manner, a portion of the video from Party A, a portion of the video from Party B, and a portion of the video of background 308 are combined and displayed together on display 306 as depicted in FIG. 3B.

If smart device 302 sends its video to smart device 202 and/or 222, Party A's display shown in FIG. 2C and/or Party B's display shown in FIG. 2D optionally are updated to include the video feed of Party C. Party A will see Party B's and Party C's video images, which gives Party A, a perception that Party B and Party C are also talking/present in the same room. The same is true of Party B. Party B will see Party A's and Party C's video images, which also gives Party B a perception that Party A and Party C are also talking/present in the same room.

The example in FIGS. 3A-3B can also be extended to a multi-party conferencing mode. In multi-party conferencing mode, based on the combination of accelerometer data (or other sensor data) and augmented video reality (AVR) technology, each user in the multiple-party conference will be able to locate other connected users according to the angle of where his/her smart device is pointing to. For example, in a 4-party conference call involving Party A, Party B, Party C and Party D, if we take Party A's point of view, Party A can locate Party B by pointing a smart device to, for example, 60 degrees toward left, or to locate Party C by, for example, pointing a smart device straight forward, or to locate the Party D by, for example, pointing a smart device to 60 degree toward right. Also, when one of the parties is located, his/her real-time selfie-video image (captured from the corresponding party's front-facing camera) will be overlaid over an image of the background. As a result, Party A can have a realistic perception that he/she is talking to Party B, Party C, and Party D in the same room by pointing his smart device to difference angles, and those parties are "located" between the smart device and the background.

Figure 4B:
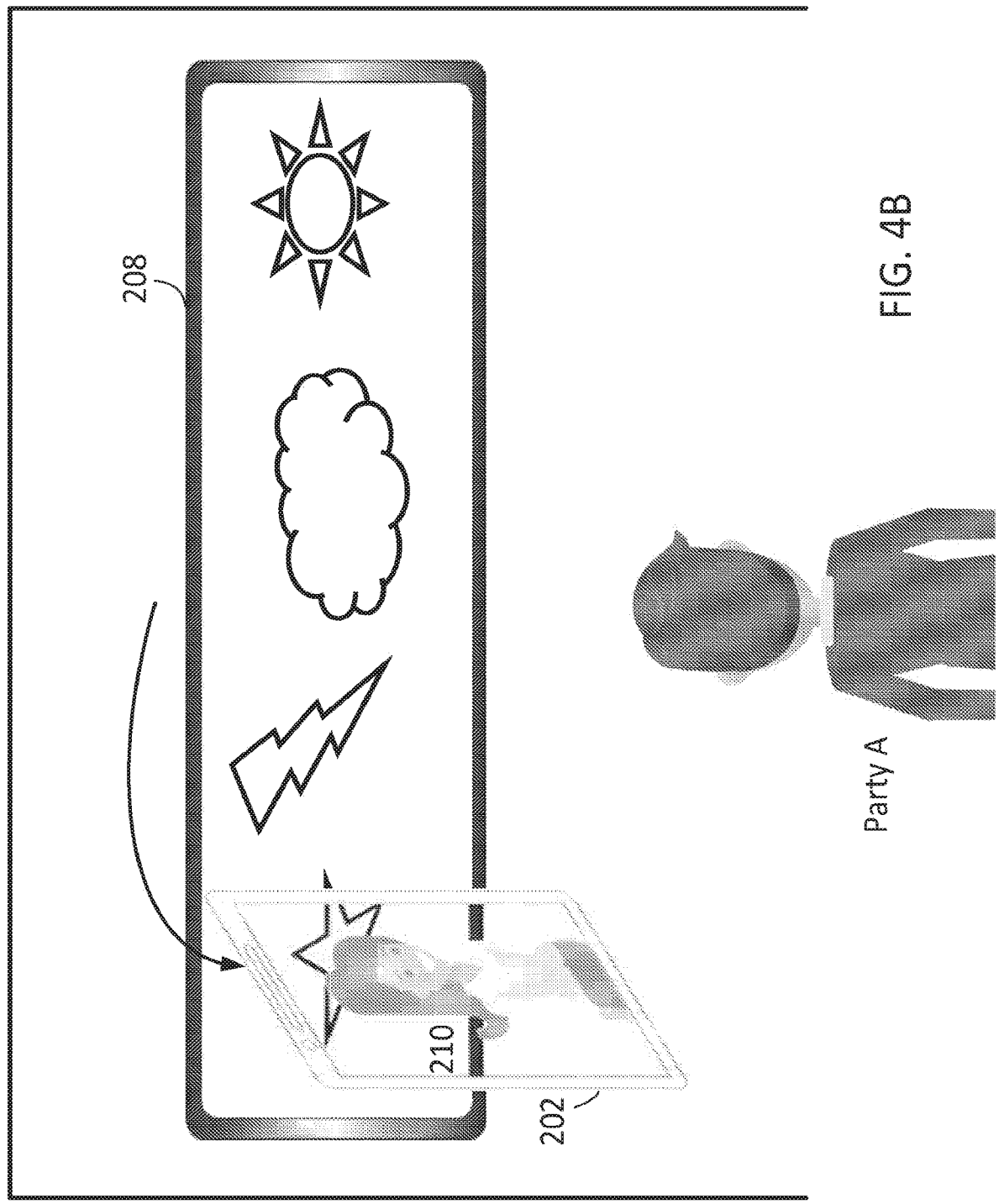

FIGS. 4A-4E (which is a different perspective of the same environment as depicted in FIGS. 2A and 2C) depict an example of this mode. FIG. 4A depicts the situation from Party A's point of view before the conference call begins. Party A looks into smart device 202 (see description with respect to FIG. 2A), which displays image 210 of background 208 captured from the back-facing camera of smart device 202. FIG. 4B illustrates the situation that, during the conference call, if Party A wants to talk to, for example, Party B, Party A would turn smart device 202 to an angle, such as 60-degree, toward the left. The trimmed video (e.g., with the background cropped out) of Party B will be shown on display 206 as between smart device 202 and background 208, so that Party A can have a perception that Party B is sitting at the left-hand side, say 60-degree, inside the room between smart device 202 and background 208. Of course, in reality Party B can be located anywhere in the world. The relevant location of Party B, against Party A, is determined by the computer process running inside (or connected to) smart device 202.

Figure 4C:
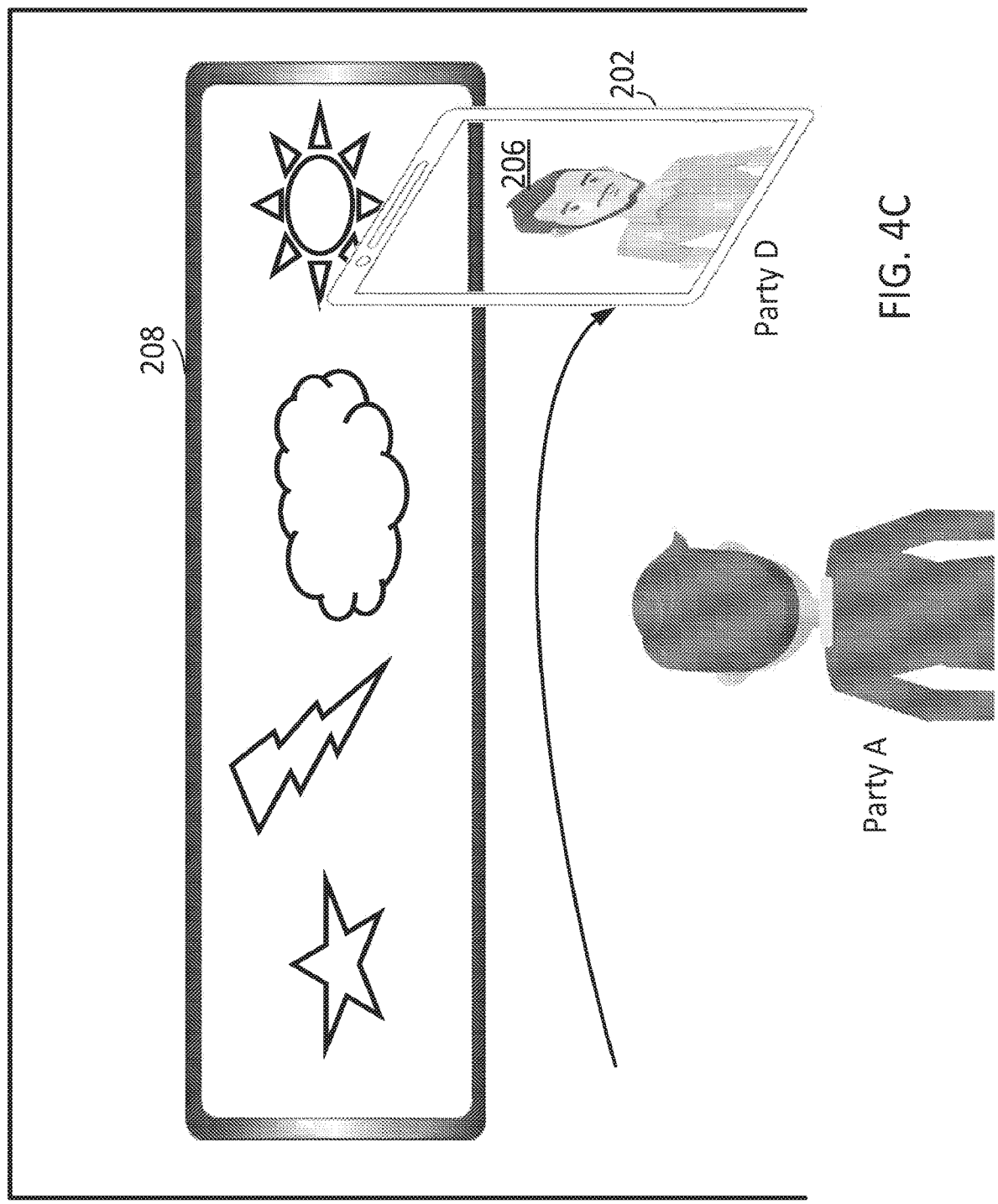

After talking to Party B, say Party A would like to talk to Party D, and Party D is located at, for example, 60-degree to the right hand side, Party A should turn smart device 202 toward that angle in order to unveil Party-D's video image overlaid over image 210 of background 208 on display 306. This idea is illustrated in FIG. 4C.

Figure 4E:
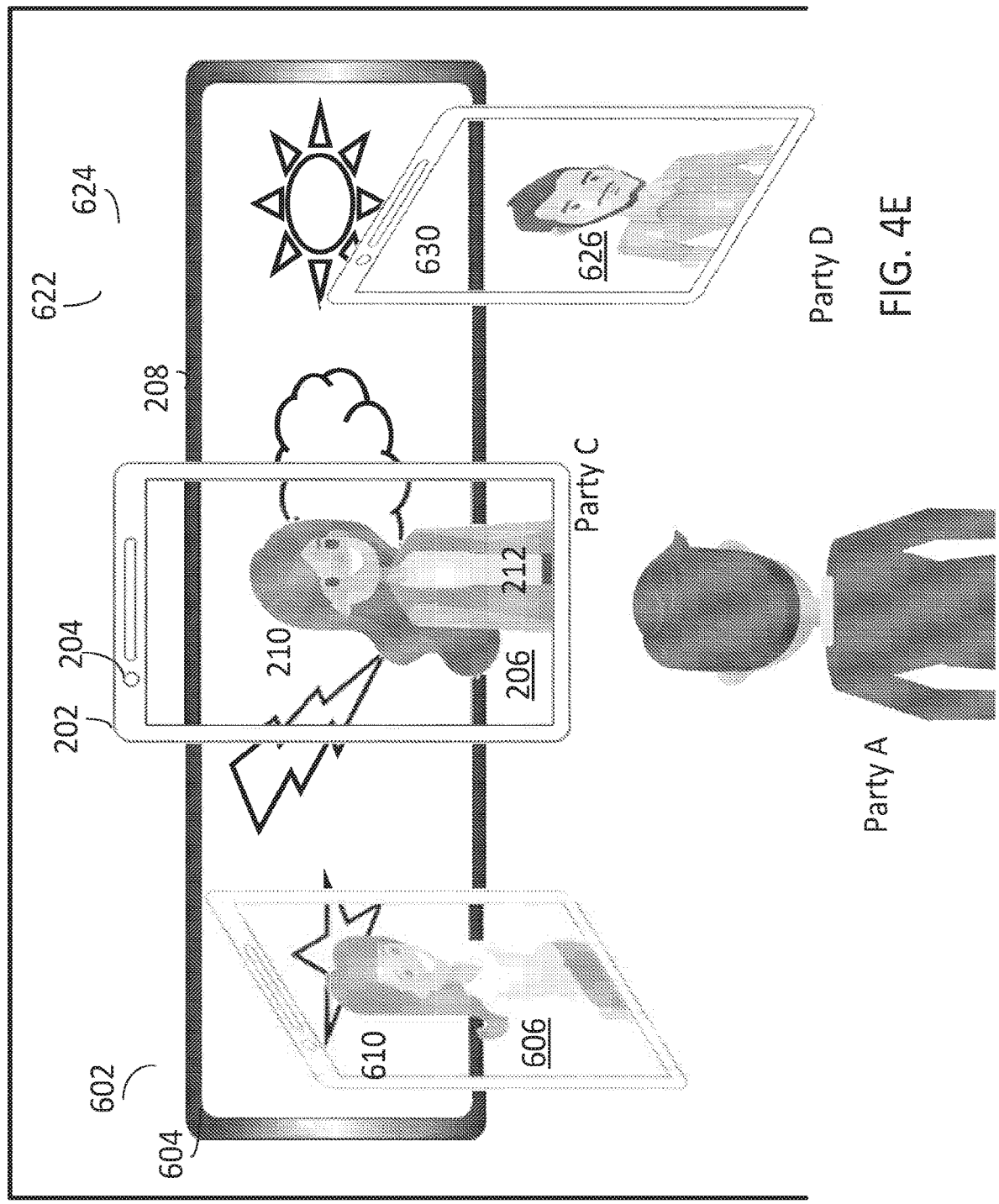

Finally, when Party A feels like talking to Party C at some moment, Party A can simply point smart device 202 straight in front to locate Party C, such as shown in FIG. 4D. Optionally, when multiple smart devices are available and placed at the right positions, Party A can actually see all other connected parties simultaneously. For example, FIG. 4E includes smart device 602 having front facing camera 604, a back facing camera, and display 606, which is showing image 610 of background 208 overlaid with a video of Party B. FIG. 4E also includes smart device 622 having front facing camera 624, a back facing camera, and display 626, which is showing image 630 of background 208 overlaid with a video of Party D.

The example above uses specific angles to change which party is displayed, other criteria can also be used to change the party. For example, instead of a specific angle, the smart device may change the party being displayed when a specific orientation change is detected (e.g., a specific orientation is held for a threshold amount of time, a range of orientations is met or held for a threshold amount of time, a threshold orientation is reached, etc.). Criteria based on other movement can also be used. For example, a position movement (e.g., 1 m translation to the left or right without rotation) may trigger the smart device to display the video from a different remote party.

Through wireless or wired networking and computer processing, one can overlay one or more remote real-time objects onto the background image and/or video of a local display, so that the viewer can perceive that the remote object(s) is right behind the display.

In this Multi-party application (e.g., online game or video conferencing), based on the combination of accelerometer data (or other sensor data) and AVR technology, each user in the multiple-party application will be able to locate other connected remote users, in a way described in claim 1, according to the angle of where his/her smart device is pointing to.

Above, video conferencing is used to illustrate some features and some advantages of some embodiments of the present technology. It should be appreciated, however, that the present technology can also be used in other contexts, such as video gaming, medicine, social networking, and other circumstances where improved and/or more immersive communication is beneficial.

Figure 5:
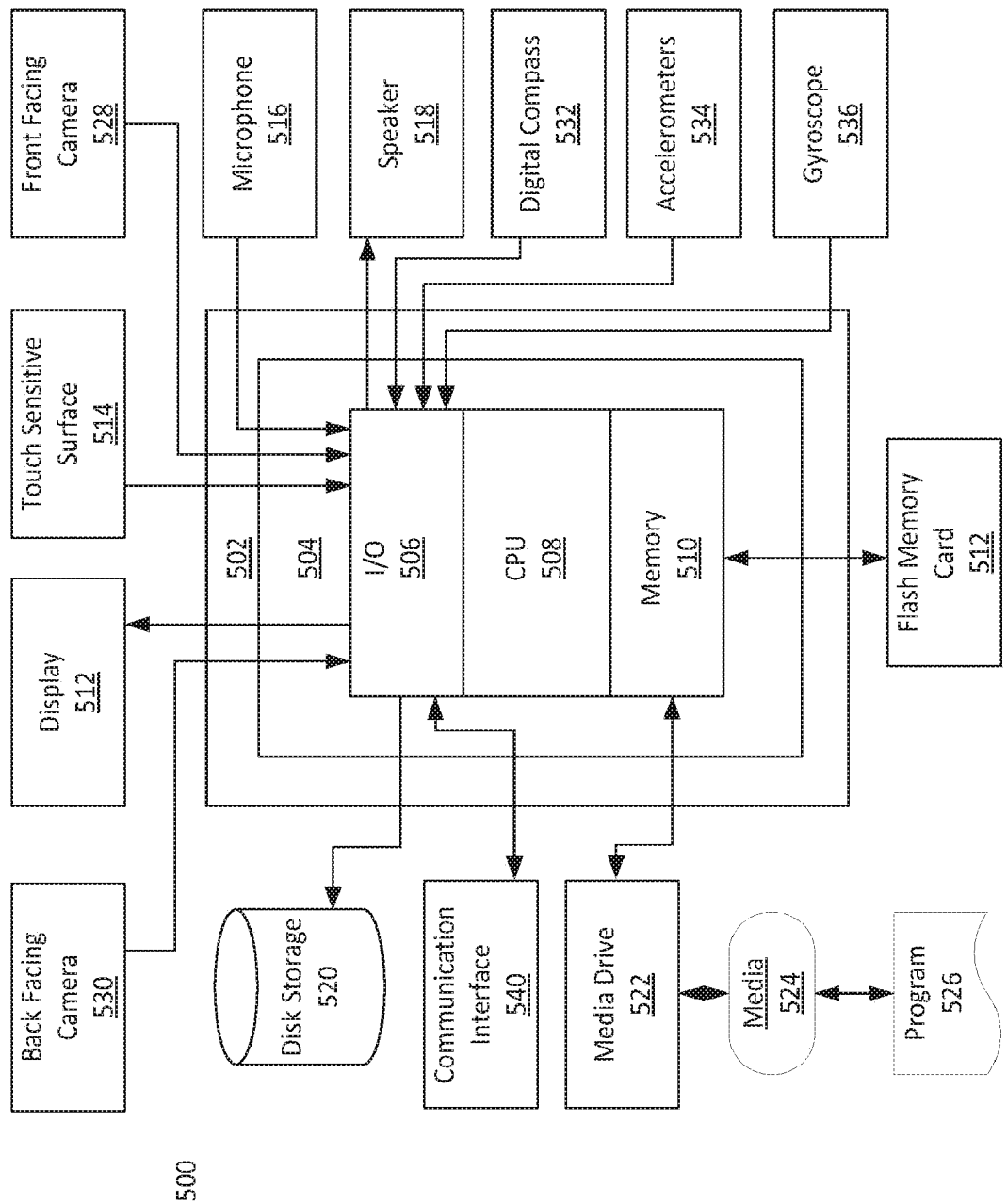
FIG. 5 depicts an exemplary device that may be used to implement embodiments of the present technology.

Turning now to FIG. 5, components of an exemplary computing system 500, configured to perform any of the above-described processes and/or operations are depicted. For example, computing system 500 may be used to implement smart device 100 described above that implements any combination of the above embodiments. Computing system 500 may include, for example, a processor, memory, storage, and input/output peripherals (e.g., display, keyboard, stylus, drawing device, disk drive, Internet connection, camera/scanner, microphone, speaker, etc.). However, computing system 500 may include circuitry or other specialized hardware for carrying out some or all aspects of the processes.

In computing system 500, the main system 502 may include a motherboard 504 with a bus that connects an input/output (I/O) section 506, one or more microprocessors 508, and a memory section 510, which may have a flash memory card 512 related to it. Memory section 510 may contain computer-executable instructions and/or data for carrying out the processes above. The I/O section 506 may be connected to display 524 (e.g., to display a view), a camera/scanner 526, a microphone 528 (e.g., to obtain an audio recording), a speaker 530 (e.g., to play back the audio recording), a disk storage unit 516, and a media drive unit 518. The media drive unit 518 can read/write a non-transitory computer-readable storage medium 520, which can contain programs 522 and/or data used to implement the techniques described above.

Additionally, a non-transitory computer-readable storage medium can be used to store (e.g., tangibly embody) one or more computer programs for performing any one of the above-described processes by means of a computer. The computer program may be written, for example, in a general-purpose programming language (e.g., Pascal, C, C++, Java, or the like) or some specialized application-specific language.

Computing system 500 may include various sensors, such as front-facing camera 530, back-facing camera 532, orientation sensors (such as, compass 534, accelerometer 536, gyroscope 538), and/or touch-sensitive surface 540. Other sensors may also be included.

While the various components of computing system 500 are depicted as separate in FIG. 5, various components may be combined together. For example, display 524 and touch sensitive surface 540 may be combined together into a touch-sensitive display.

Computing system 500 may also include communication interface 540. This interface includes one or more interfaces for communicating information with other computing systems. For example communication interface 540 optionally includes one or more of a wireless interface (e.g., WiFi, 802.11, Bluetooth, 5 G, LTE, etc.), wired interface (USB, Ethernet, Thunderbolt, etc.), or other type of interface (e.g., IR).

Various exemplary embodiments are described herein. Reference is made to these examples in a non-limiting sense. They are provided to illustrate more broadly applicable aspects of the disclosed technology. Various changes may be made and equivalents may be substituted without departing from the true spirit and scope of the various embodiments. In addition, many modifications may be made to adapt a particular situation, material, composition of matter, process, process act(s) or step(s) to the objective(s), spirit or scope of the various embodiments. Further, as will be appreciated by those with skill in the art, each of the individual variations described and illustrated herein has discrete components and features which may be readily separated from or combined with the features of any of the other several embodiments without departing from the scope or spirit of the various embodiments.

Exemplary methods, non-transitory computer-readable storage media, systems, and electronic devices are set out in the following items:

1. A method, comprising:
at an electronic device coupled to a display, a communication interface, and a first image sensor:
   capturing first image data from the first image sensor;
   receiving second image data over the communication interface from a first remote device; and
   displaying on the display a portion of the second image data with a portion of the first image data, wherein displayed portion of the second image data obscures some of the first image data.

2. The method of item 1, wherein the electronic device is further coupled to a second image sensor pointing in a different direction than a direction of the first image sensor, the method further comprising:
   capturing third image data from the second image sensor; and
   sending the third image data to the first remote device over the communication interface.

3. The method of item 2, wherein the second image sensor faces the same direction as the display faces.

4. The method of any one of items 1 to 3 further comprising:
   cropping the second image data.

5. The method of any one of items 1-4, the method further comprising:
   capturing fourth image data from the first image sensor;
   receiving fifth image data over the communication interface from a second external device;
   in response to detecting movement of the electronic device, replacing display of the portion of the second image data and portion of the first image data with display of a portion of the fifth image data with a portion of the fourth image data.

6. The method of any one of items 1-5 wherein the display, the communication interface, and the first image sensor are all contained within the same electronic device housing.

7. The method of any one of items 1-5 wherein at least one of the display, the communication interface, or the first image sensor are not contained within the same housing.

8. A non-transitory computer-readable storage medium encoded with a computer program executable by an electronic device coupled to a display, memory, and an image sensor, the computer program comprising instructions for:
   capturing first image data from the first image sensor;
   receiving second image data over the communication interface from a first remote device; and
   displaying on the display a portion of the second image data with a portion of the first image data, wherein displayed portion of the second image data obscures some of the first image data.

9. The computer-readable storage medium of item 8, wherein the electronic device is further coupled to a second image sensor pointing in a different direction than a direction of the first image sensor, the computer program comprising instructions for:

capturing third image data from the second image sensor; and sending the third image data to the first remote device over the communication interface.

10. The computer-readable storage medium of item 9, wherein the second image sensor faces the same direction as the display faces.

11. The computer-readable storage medium of any one of items 8 to 10 the computer program comprising instructions for:

cropping the second image data; and merging the cropped second image data with the first image data.

12. The computer-readable storage medium of any one of items 8-11, the computer program comprising instructions for:

capturing fourth image data from the first image sensor;

receiving fifth image data over the communication interface from a second external device;

in response to detecting movement of the electronic device, replacing display of the portion of the second image data and portion of the first image data with display of a portion of the fifth image data with a portion of the fourth image data.

13. The computer-readable storage medium of any one of items 8-12 wherein the display, the communication interface, and the first image sensor are all contained within the same electronic device housing.

14. The computer-readable storage medium of any one of items 8-12 wherein at least one of the display, the communication interface, or the first image sensor are not contained within the same housing.

15. A system comprising:

a display;

an image sensor, and memory encoded with a computer program executable by an electronic device coupled to a display, memory, and an image sensor, the computer program having instructions for:

capturing first image data from the first image sensor;

receiving second image data over the communication interface from a first remote device; and displaying on the display a portion of the second image data with a portion of the first image data, wherein displayed portion of the second image data obscures some of the first image data.

16. The system of item 15, wherein the electronic device is further coupled to a second image sensor pointing in a different direction than a direction of the first image sensor, the computer program comprising instructions for:

capturing third image data from the second image sensor; and sending the third image data to the first remote device over the communication interface.

17. The system of item 16, wherein the second image sensor faces the same direction as the display faces.

18. The system of any one of items 15 to 17 the computer program comprising instructions for:

cropping the second image data.

19. The system of any one of items 15-18, the computer program comprising instructions for:

capturing fourth image data from the first image sensor;

receiving fifth image data over the communication interface from a second external device;

in response to detecting movement of the electronic device, replacing display of the portion of the second image data and portion of the first image data with display of a portion of the fifth image data with a portion of the fourth image data.

20. The system any one of items 15-18 wherein the display, the communication interface, and the first image sensor are all contained within the same electronic device housing.

21. The system of any one of items 15-18 wherein at least one of the display, the communication interface, or the first image sensor are not contained within the same housing.

What is claimed is:

1. A method, comprising:

at an electronic device coupled to a display facing toward front of the electronic device, a communication interface, and a first image sensor facing toward back of the electronic device:

capturing first image data from the first image sensor, the first image data representing the environment surrounding the electronic device;

receiving second image data over the communication interface from a first remote device, wherein the second image data is real-time video data of a first remote user of the first remote device;

cropping the second image data to obtain a cropped image data; and displaying on the display the cropped image data with a portion of the first image data, wherein the cropped image data obscures some of the first image data such that the display shows the first remote user of the first remote device appearing in the environment surrounding the electronic device;

receiving third image data over the communication interface from a second remote device, wherein the third image data is real-time video data of a second remote user of the second remote device; and detecting a position change of the electronic device using a sensor;

capturing updated first image data form the first image sensor; and in response to detecting the position change, updating the display to display the third image data overlaid on the updated first image data such that the display shows the second remote user of the second remote device appearing in the environment surrounding the electronic device.

2. The method of claim 1, wherein the electronic device is further coupled to a second image sensor pointing in a different direction than a direction of the first image sensor, the method further comprising:

capturing fourth image data from the second image sensor; and sending the fourth image data to the first remote device over the communication interface.

3. The method of claim 2, wherein the second image sensor faces the same direction as the display faces.

4. The method of claim 1 wherein the display, the communication interface, and the first image sensor are all contained within the same electronic device housing.

5. The method of claim 1 wherein at least one of the display, the communication interface, or the first image sensor are not contained within the same housing.

6. A non-transitory computer-readable storage medium encoded with a computer program executable by an electronic device coupled to a display facing toward front of the electronic device, memory, and an image sensor facing toward back of the electronic device, the computer program comprising instructions for:
- capturing first image data from the first image sensor, the first image data representing the environment surrounding the electronic device;
- receiving second image data over the communication interface from a first remote device, wherein the second image data is real-time video data of a first remote user of the first remote device;
- cropping the second image data to obtain a cropped image data; and
- displaying on the display the cropped image data with a portion of the first image data, wherein the cropped image data obscures some of the first image data such that the display shows the first remote user of the first remote device appearing in the environment surrounding the electronic device;
- receiving third image data over the communication interface from a second remote device, wherein the third image data is real-time video data of a second remote user of the second remote device; and
- detecting a position change of the electronic device using a sensor;
- capturing updated first image data form the first image sensor; and
- in response to detecting the position change, updating the display to display the third image data overlaid on the updated first image data such that the display shows the second remote user of the second remote device appearing in the environment surrounding the electronic device.

7. The computer-readable storage medium of claim 6, wherein the electronic device is further coupled to a second image sensor pointing in a different direction than a direction of the first image sensor, the computer program comprising instructions for:
- capturing fourth image data from the second image sensor; and
- sending the fourth image data to the first remote device over the communication interface.

8. The computer-readable storage medium of claim 7, wherein the second image sensor faces the same direction as the display faces.

9. The computer-readable storage medium of claim 6 the computer program comprising instructions for:
- merging the cropped image with the first image data.

10. The computer-readable storage medium of claim 6 wherein the display, the communication interface, and the first image sensor are all contained within the same electronic device housing.

11. The computer-readable storage medium of claim 6 wherein at least one of the display, the communication interface, or the first image sensor are not contained within the same housing.

12. A system comprising:
- a display facing toward front of the electronic device;
- an image sensor facing toward back of the electronic device; and
- memory encoded with a computer program executable by an electronic device coupled to a display, memory, and an image sensor, the computer program having instructions for:
  - capturing first image data from the first image sensor, the first image data representing the environment surrounding the electronic device;
  - receiving second image data over the communication interface from a first remote device, wherein the second image data is real-time video data of a first remote user of the first remote device;
  - cropping the second image data to obtain a cropped image data;
  - displaying on the display the cropped image data with a portion of the first image data, wherein the cropped image data obscures some of the first image data such that the display shows the first remote user of the first remote device appearing in the environment surrounding the electronic device;
  - receiving third image data over the communication interface from a second remote device, wherein the third image data is real-time video data of a second remote user of the second remote device; and
  - detecting a position change of the electronic device using a sensor;
  - capturing updated first image data form the first image sensor; and
  - in response to detecting the position change, updating the display to display the third image data overlaid on the updated first image data such that the display shows the second remote user of the second remote device appearing in the environment surrounding the electronic device.

13. The system of claim 12, wherein the electronic device is further coupled to a second image sensor pointing in a different direction than a direction of the first image sensor, the computer program comprising instructions for:
- capturing fourth image data from the second image sensor; and
- sending the fourth image data to the first remote device over the communication interface.

14. The system of claim 13, wherein the second image sensor faces the same direction as the display faces.

15. The system of claim 12 wherein the display, the communication interface, and the first image sensor are all contained within the same electronic device housing.

* * * * *